United States Patent
Walters et al.

[11] Patent Number: 6,048,640
[45] Date of Patent: Apr. 11, 2000

[54] ELECTRODE PACKAGE AND METHOD FOR SEALING SAME

[75] Inventors: Warren R. Walters, Lakeville, Minn.; Michael J. Luhrs, Des Moines, Iowa

[73] Assignee: Katecho, Inc., Des Moines, Iowa

[21] Appl. No.: 09/085,901

[22] Filed: May 27, 1998

[51] Int. Cl.[7] .............................. H01M 2/18; B65D 85/00
[52] U.S. Cl. .......................... 429/136; 29/623.2; 206/701; 206/727; 206/726; 206/728; 206/438
[58] Field of Search ...................... 429/121, 124, 429/127, 136; 29/623.2; 206/701

[56] References Cited

U.S. PATENT DOCUMENTS

| | | | |
|---|---|---|---|
| 4,040,412 | 8/1977 | Sato | 128/2.06 E |
| 4,078,553 | 3/1978 | Duroux | 128/2.1 Z |
| 4,390,384 | 6/1983 | Turner | 156/221 |
| 5,234,473 | 8/1993 | Piper et al. | 429/185 |
| 5,402,884 | 4/1995 | Gilman et al. | |
| 5,579,919 | 12/1996 | Gilman et al. | 206/701 |
| 5,755,763 | 5/1998 | Farfel | 607/122 |
| 5,916,244 | 6/1999 | Walters | 607/142 |

Primary Examiner—Maria Nuzzolillo
Assistant Examiner—Angela J. Martin
Attorney, Agent, or Firm—Zarley, McKee, Thomte, Voorhees & Sease

[57] ABSTRACT

An electrode package includes a pouch having pouch walls forming a sealed pouch enclosure. At least one electrode is within the pouch enclosure and includes an electrode wire having one end connected to the electrode within the pouch, an intermediate portion extending through the pouch walls, and a second end outside the pouch enclosure. A sealing joint is formed at the point where the intermediate portion of the wire extends through the pouch walls. The pouch walls have a plastic layer which surrounds and contacts the intermediate portion of the wire at the sealing joint to form an air tight seal. The invention also includes a method whereby heat and pressure are applied at the sealing joint to cause the plastic layer of the pouch walls to melt and fuse around the wires to create the seal.

3 Claims, 9 Drawing Sheets

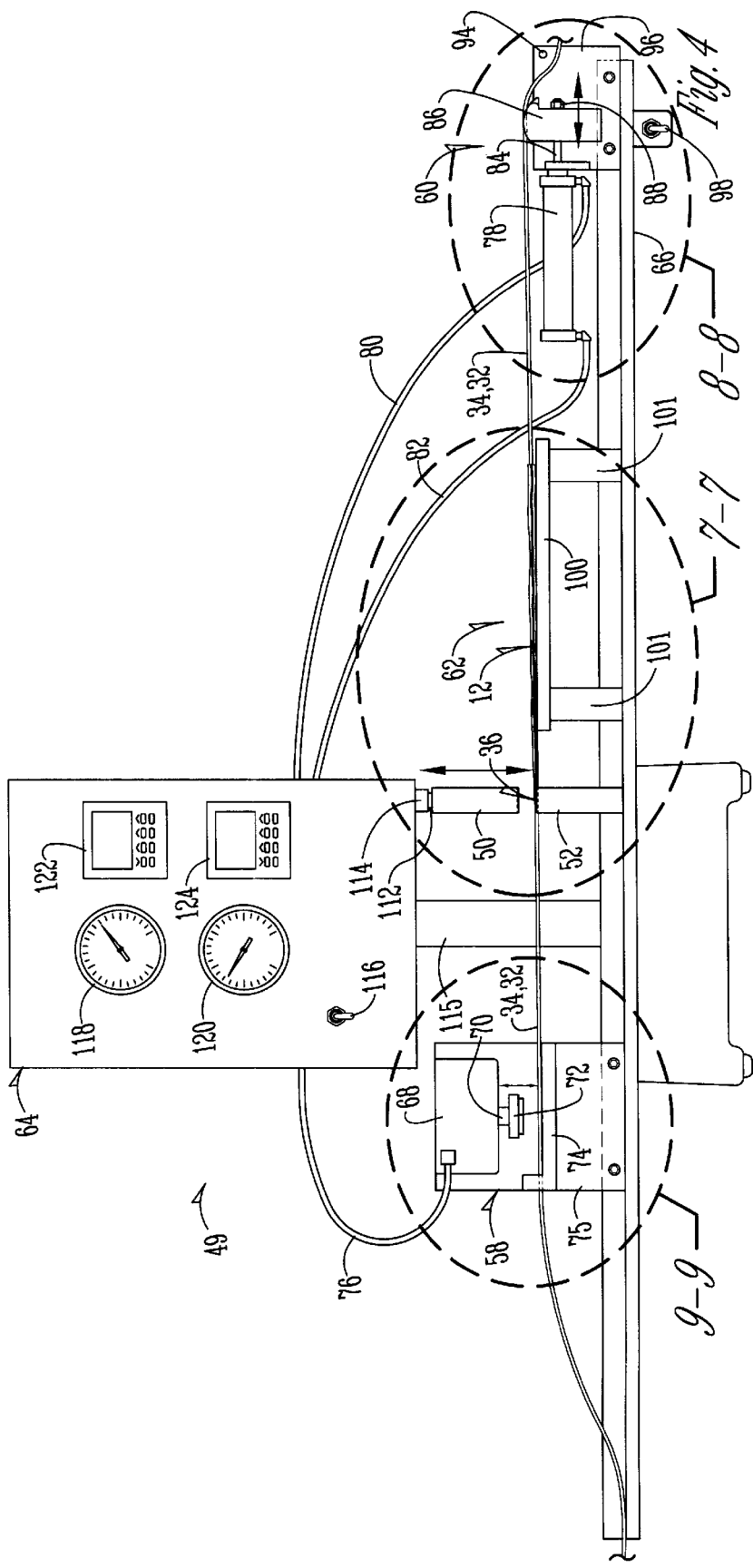

ELECTRODE PACKAGE AND METHOD FOR SEALING SAME

BACKGROUND OF THE INVENTION

The present invention relates to an electrode package and a method for sealing same. Specifically it pertains to an electrode package containing electrodes having wires which extend through the wall of the package to the exterior of the package, and having a unique seal at the point where the wires pass through the wall of the package.

Physiological electrodes have been used for various functions, including defibrillating patients whose hearts are in fibrillation, monitoring the heart beat of patients, pacing the heart beat of patients, and other types of heart and muscle stimulation. The electrodes generally are placed on the chest of the patient and include wires extending to a console which controls the particular function desired.

These electrodes are stored in hermetically sealed packages so as to maintain their performance until the time of use. At the time of use, the person applying the electrodes must tear open the package, remove the electrodes from the package, place them on the patient's chest, and plug the wire into the console.

Because time is often critical, particularly in cases where the patient is encountering fibrillation, it is desirable to reduce the time necessary to remove the electrodes from the package and make them operable.

One way of reducing the time necessary to make the electrodes operable is to provide a package having the electrodes within the package, but having the wires extending through the walls of the package to a plug which is outside the package. This enables the operator to plug the plug into the console before an emergency arises. Then when the electrodes are needed, the operator need only tear open the package, pull the electrodes out of the package and place them on the chest of the patient. Because the wires are already plugged into the console, the system is ready for defibrillation or monitoring or any other function needed.

Extending the wires through the hermetically sealed package, while at the same time maintaining the hermetic seal of the package, presents a difficult problem, particularly in the manufacture of the packaged electrode. Different methods have been tried for providing a proper seal. One method is to make the package from two facing sheet members that are sealed around their perimeters. The wire is extended through the seal, and a paper and glue seal are manually fused around the point where the wires extend out of the package. Manual application of the paper and glue to the seal, together with the required heating and curing of the glue, consume a considerable amount of time during manufacture, and therefore increase the price of the electrodes substantially.

Another prior art method used for creating a seal is to place a plastic member, called a football, around the wires. Then the football is placed between the sheet members of the pouch at the point where the wires exit the pouch. The football is presealed around the wires initially, and after it is placed between the sheet members, heat and pressure are applied to provide a seal between the football and the two sheet members. While this particular method is less time consuming, it is more expensive because it requires the cost of the football, an added part, and because it requires the football to be presealed around the wires, thereby adding an additional step to the sealing process.

Therefore a primary object of the present invention is the provision of an improved electrode package and method for sealing same.

A further object of the present invention is the provision of an improved seal around the wires as they pass through the electrode package without requiring additional parts such as a sealing football, and without requiring the need of a special paper and glue seal.

A further object of the present invention is the provision of an electrode package and method for sealing same which provides a seal where the wires exit the package within a minimum amount of time.

A further object of the present invention is the provision of an improved seal where the wires exit the package which utilizes the inherent materials of the package and the wire insulation to create a seal.

A further object of the present invention is the provision of an improved electrode package and method for sealing same which requires merely the application of heat and pressure to create the seal.

A further object of the present invention is the provision of an improved electrode package and method for sealing same which involves simple and efficient means of manufacture and which is durable in use.

SUMMARY OF THE INVENTION

The foregoing objects may be achieved by a combination which includes a pouch having at least first and second pouch walls joined together at a seam to form a sealed pouch enclosure. At least one electrode is within the pouch enclosure and includes an electrical wire having a first end connected to the electrode within the pouch, an intermediate portion extending through the pouch wall, and a second end outside the pouch enclosure. A sealing joint is provided at the point where the intermediate portion of the wire extends through the pouch wall. The sealing joint provides an air tight seal around the intermediate portion of the wire. Each of the first and second pouch walls have a plastic layer, and the plastic layers of those pouch walls surround and contact the intermediate portion of the wire at the sealing joint to form an air tight seal.

The method for sealing the electrode within the pouch comprises applying heat and pressure to the wire and the pouch at the sealing point until the plastic layer at least partially melts and fuses around the wire to create a seal between the walls of the pouch and the wire.

The preferred method includes applying sufficient heat and pressure to cause both the plastic layer of the pouch walls and plastic insulation surrounding the wire to at least partially melt and fuse together to create the seal between the walls of the pouch and the wire.

The preferred method for applying heat and pressure is the use of dies which are placed on opposite sides of the sealing point and which are compressed together so as to cause the formation of the seal.

In one form of the method at least one of the dies is heated to a predetermined temperature so as to impart heat to the walls of the pouch and the wire during the compressing step.

BRIEF DESCRIPTION OF THE FIGURES OF THE DRAWINGS

FIG. 4 is a view similar to FIG. 3, but showing the two clamps and the dies in their unclamped position.

DETAILED DESCRIPTION OF THE PREFERRED EMBODIMENT

Figure 1:
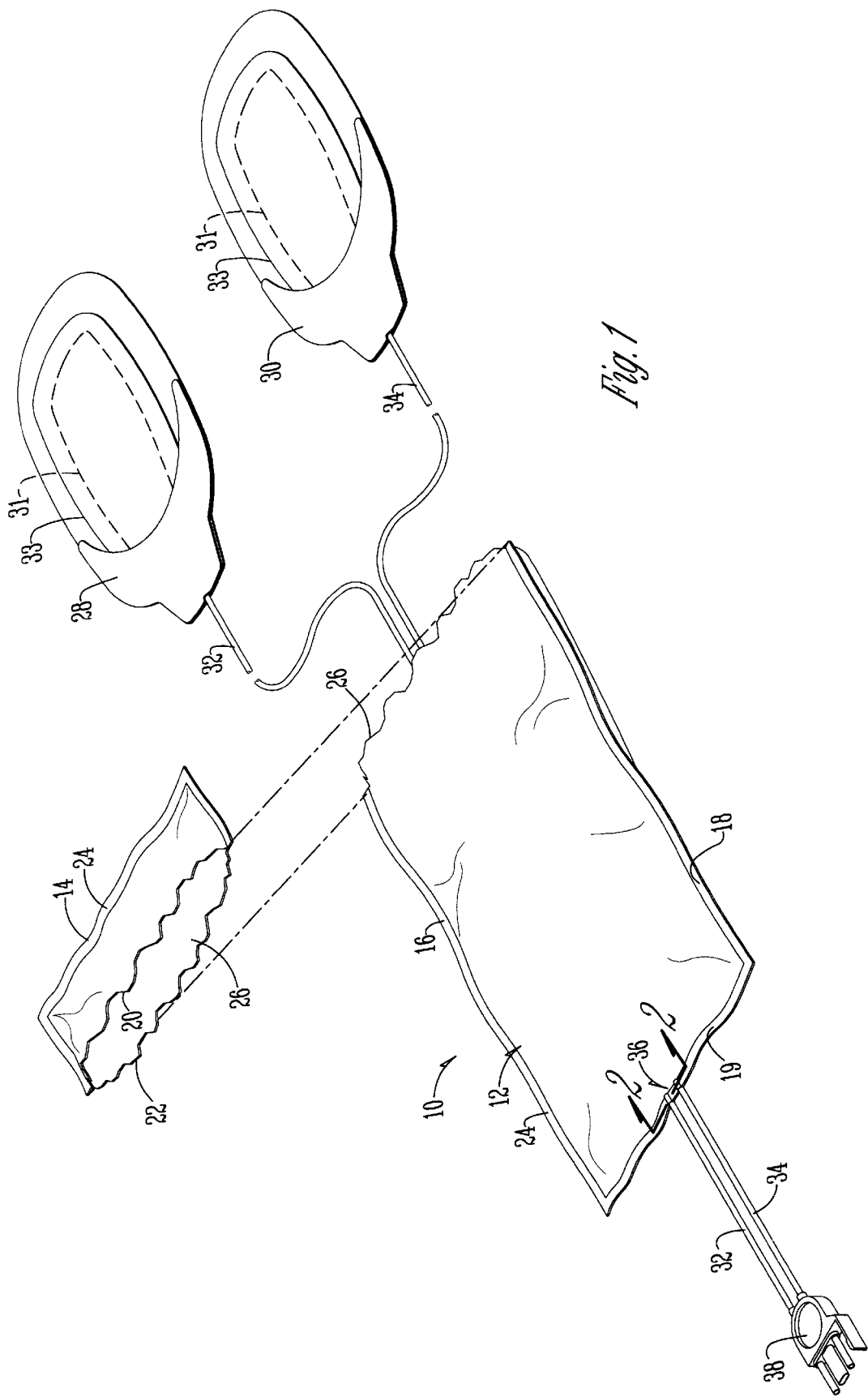
FIG. 1 is a perspective view of the pouch containing the electrodes, showing one end of the pouch removed, and the electrodes being removed from the interior of the pouch.

Referring to FIG. 1 the numeral 10 generally designates the electrode and package assembly of the present invention. Assembly 10 includes a pouch 12 having a first end 14 (shown torn off and removed in FIG. 1), opposite sides 16, 18, and a second end 19.

The pouch is formed by an upper wall 20 and a lower wall 22 which are sealed together around their perimeters by a perimeter seal 24, thereby creating a sealed cavity 26.

Within sealed cavity 26 are a first electrode 28 and a second electrode 30. While FIG. 1 shows two electrodes within the cavity, there may be only one, or there may be more than two, depending upon the particular type of electrode and its intended function. In FIG. 1 electrodes 28, 30 are defibrillating-monitoring electrodes which contain a metal foil 31 covered by a conductive hydrogel 33. Connected to the metal foil 31 of first electrode 28 and extending therefrom is a first electrode wire 32. A second electrode wire 34 is connected to the metal foil 31 of second electrode 30. Electrode wires 32, 34 extend within the cavity 26 of the pouch 12 and extend through the walls of the pouch 12 at a wire seal area 36. The wires 32, 34 terminate in a plug 38 which is outside the pouch 12 and which is adapted to be plugged into a console (not shown) for operating the electrodes 28, 30.

Figure 2:
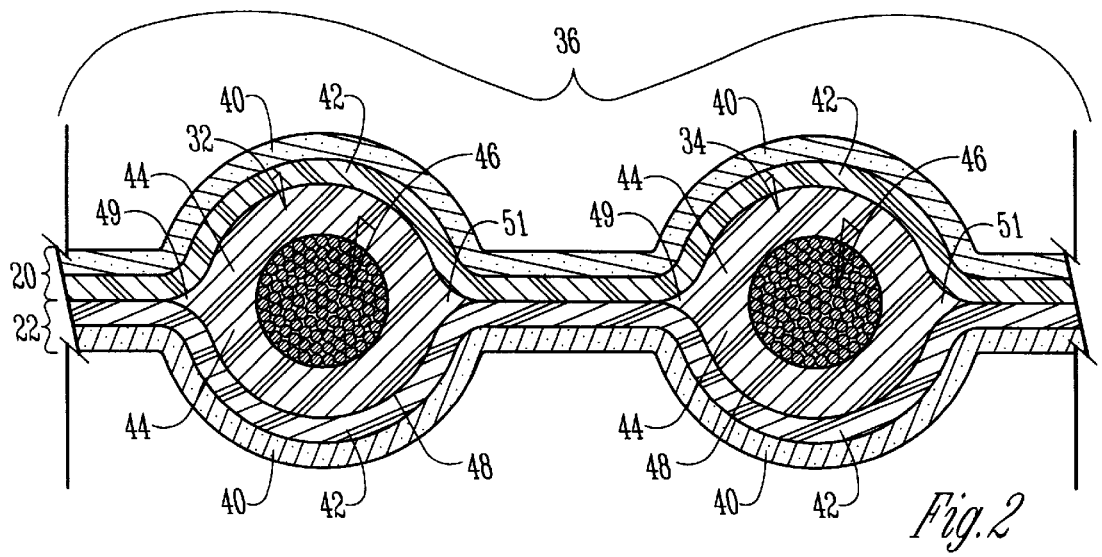
FIG. 2 is a sectional view taken along line 2—2 of FIG. 1.
Figure 5:
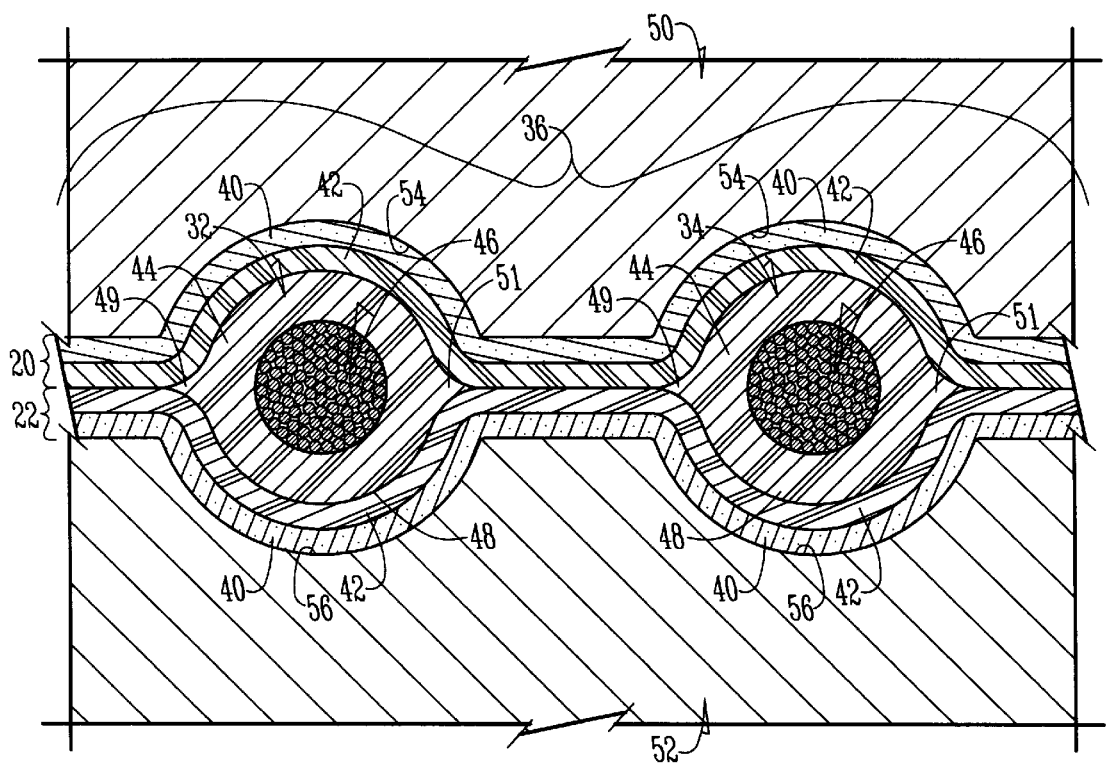
FIG. 5 is a sectional detail view taken along line 5—5 of FIG. 3.
Figure 10:
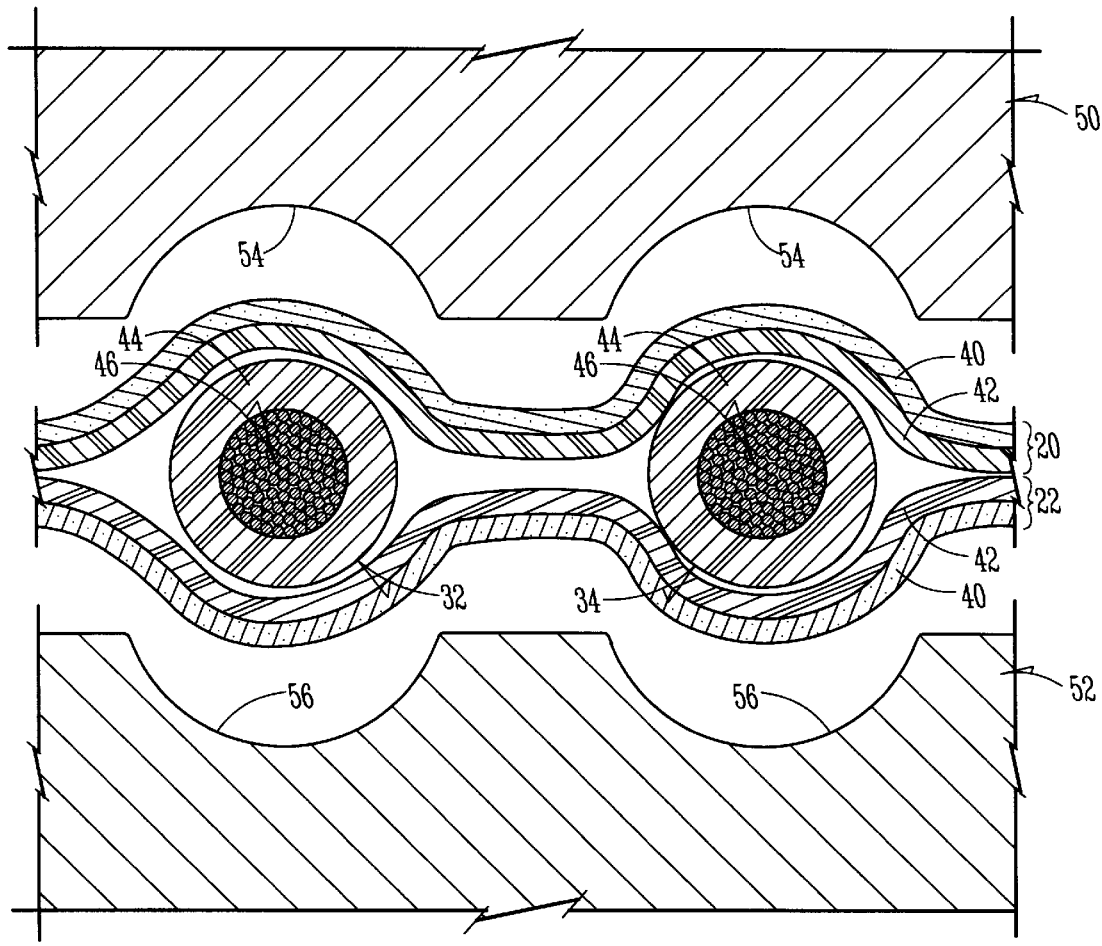
FIG. 10 is an exploded sectional view showing the dies, the pouch walls, and the wires before sealing.

Upper wall 20 and lower wall 22 are each comprised of an outer layer 40 and an inner plastic layer 42 (FIGS. 2 and 10). Wires 32, 34 are each comprised of an inner wire core 46 surrounded by a wire insulation 44. The wire cores 46 may vary from multiple wire strands as shown in FIG. 2, to solid wire cores without detracting from the invention.

The numeral 48 refers to the interface between the insulation 44 and the plastic layer 42 of the upper and lower pouch walls 20, 22. This interface 48 has been melted by the process to be described hereafter, and creates a fused interface between the walls 20, 22 and the wires 32, 34. This seal prevents the entry of air, bacteria, or other contaminates into the interior of the pouch 12 through the sealing area 36. The interface 48 does not include any added materials such as glue, paper, or other plastic parts for enhancing the seal. The seal at interface 48 is formed merely by the application of heat and pressure to cause the plastic layer 42 to melt and fuse around the wire. In some applications, the plastic insulation 44 of the wire also may be melted so that it contributes to the fusing between the layer 42 and the insulation 44. However, the melting of the insulation 44 is not believed to be essential to the proper sealing at the interface 48. FIG. 2 shows a slight deformation of the insulation material at the points 49, 51 which further facilitates the fused seal at the interface 48.

When initially packaged, the wires 32, 34 are passed through the sealing area 36 between the upper wall 20 and the lower wall 22. Then heat and pressure is applied at the sealing area 36 to cause the plastic layer 42 of the upper and lower walls 20, 22 to melt and fuse around the wires 32, 34 to create the seal. In some applications the insulation 44 of the wires 32, 34 is also melted and fuses with the plastic layer 42, while at the same time deforming to create the deformed areas 49, 51. The electrodes 28, 30 are then placed within the cavity 26 of pouch 12, and the sealed area 24 at the first end 14 of the pouch 12 is sealed in conventional manner.

When the electrode is used in an emergency situation such as an emergency room of a hospital or in an ambulance, the plug 38 can be plugged into the monitor while the package 12 is maintained in its sealed condition. When a need for the electrode arises, the operator merely tears off the first end 14, and removes the electrodes 28, 30 from the package as shown in FIG. 1. The electrodes can then be placed on the chest of the patient, and the electrodes are ready for operation. This eliminates the need for also plugging the plug 38 into the monitor at the time of use. By plugging the plug 38 into the monitor in advance, considerable time is saved during the use of the electrodes, and this savings in time can result in improved results, and possibly even the saving of a life of a patient in an emergency situation.

Referring to FIG. 4–10, an instrument 49 is shown for accomplishing the seal between the wires and the walls of the pouch. Instrument 49 includes an upper die 50 and a lower die 52 which are shown in more detail in FIGS. 5 and 10. Upper die 50 includes an upper die recess 54 and lower die 52 includes a lower die recess 56. These die recesses are shaped to have a diameter which is 0.002 inches smaller than the outer diameter of the wires (including insulation) being sealed. By choosing this relationship of the die cavities or recesses to the wire, it is possible to achieve the proper compression when the two dies are closed around the wire. Both of the upper and lower dies 50, 52 may be heated, or only one of those dies, either upper dies 50 or lower die 52, may be heated.

When the dies 50, 52 are pressed together around the wires 20, 22, they impart heat and pressure to the wires and to the plastic layer 42 of the pouch walls, thereby causing the plastic layer 42 of the pouch walls to fuse at interface 48 and provide a hermetic seal around the wires 20, 22. As used herein, the term "fuse" is intended to mean that the pouch walls form a seal around the wire and includes such a seal being formed by adhesion, chemical or mechanical bonding, or any other phenomena produced as a result of heat and pressure to form a seal.

Referring again to FIGS. 3 and 4, instrument 49 includes a left clamping station 58, a right clamping station 60, a die station 62, and a control console 64. A support frame 66 supports all of the above components.

The left holding station 58 includes a pneumatic cylinder 68 having a reciprocating ramrod 70 with a clamping surface 72 at its lower end. A clamping platform 74 is positioned below the clamping surface 72 and is mounted on the clamping frame 75 which is attached to the support frame 66. A pneumatic tube 76 is connected to cylinder 68 to provide action of the clamping surface between its upward and downward positions.

Figure 3:
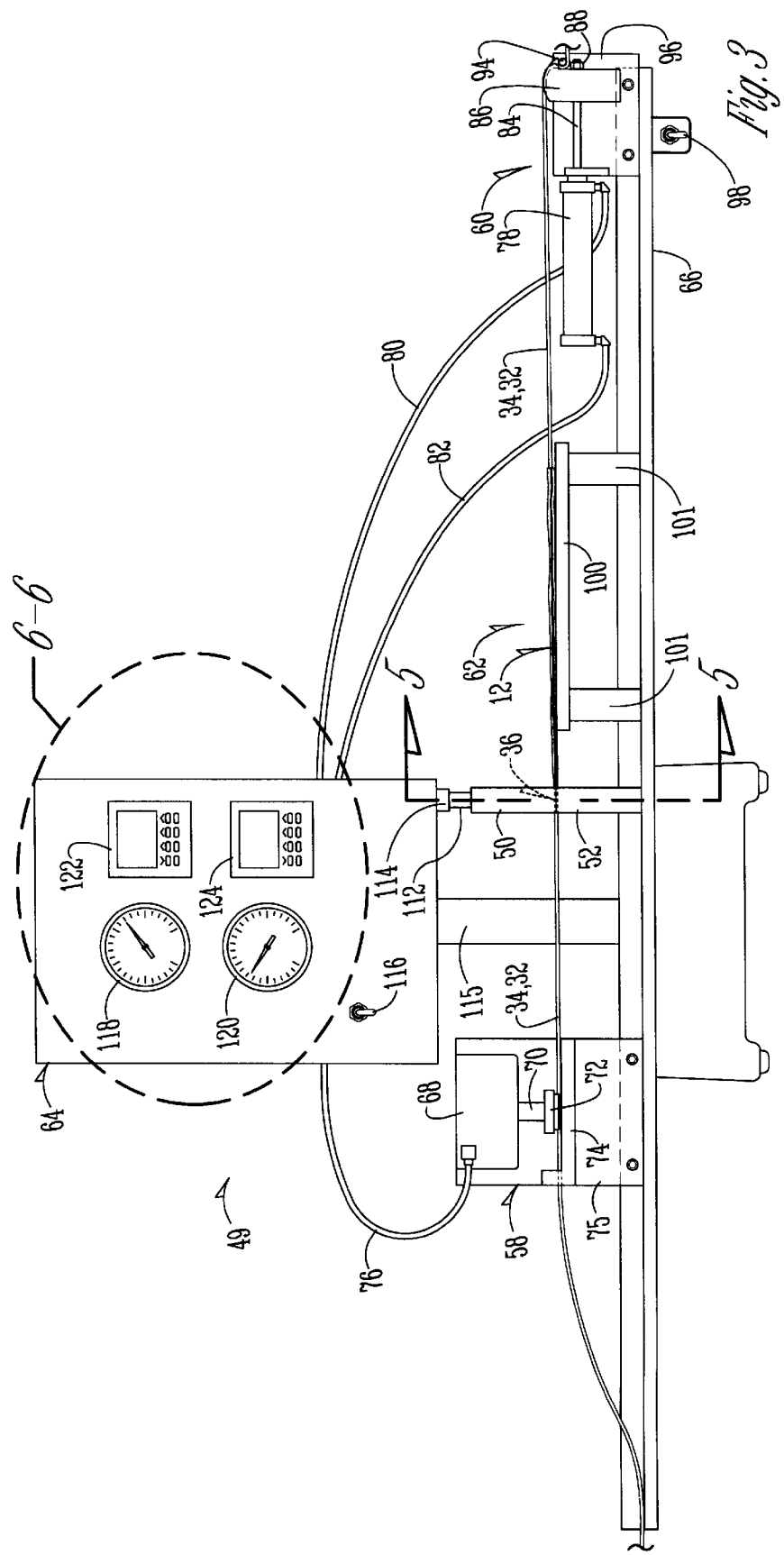
FIG. 3 is a front elevational view of the instrument for performing the sealing function around the wire, showing the two clamps and the two dies in their clamped position.
Figure 6:
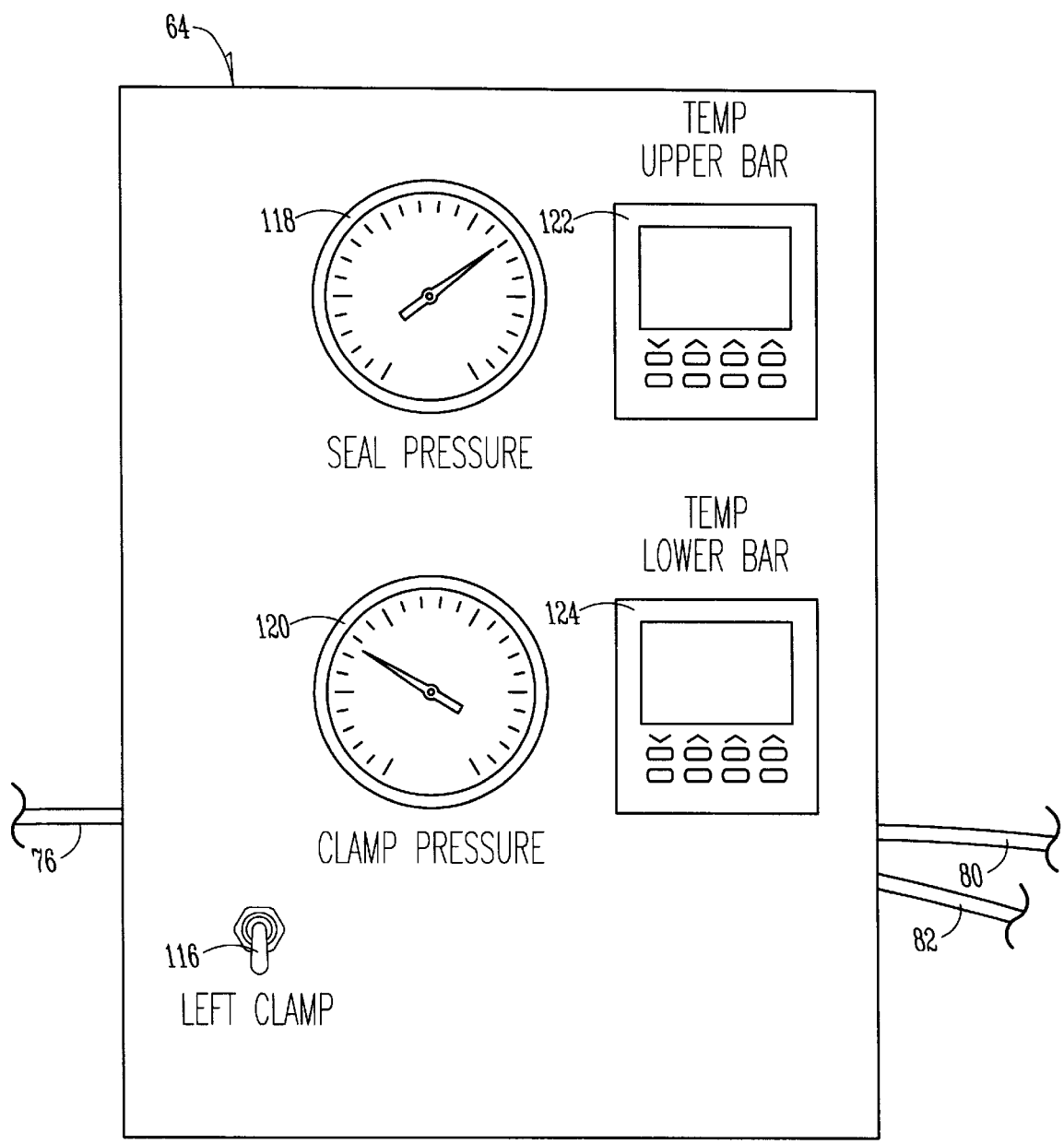
FIG. 6 is an enlarged view of the control console surrounded by line 6—6 of FIG. 3.
Figure 7:
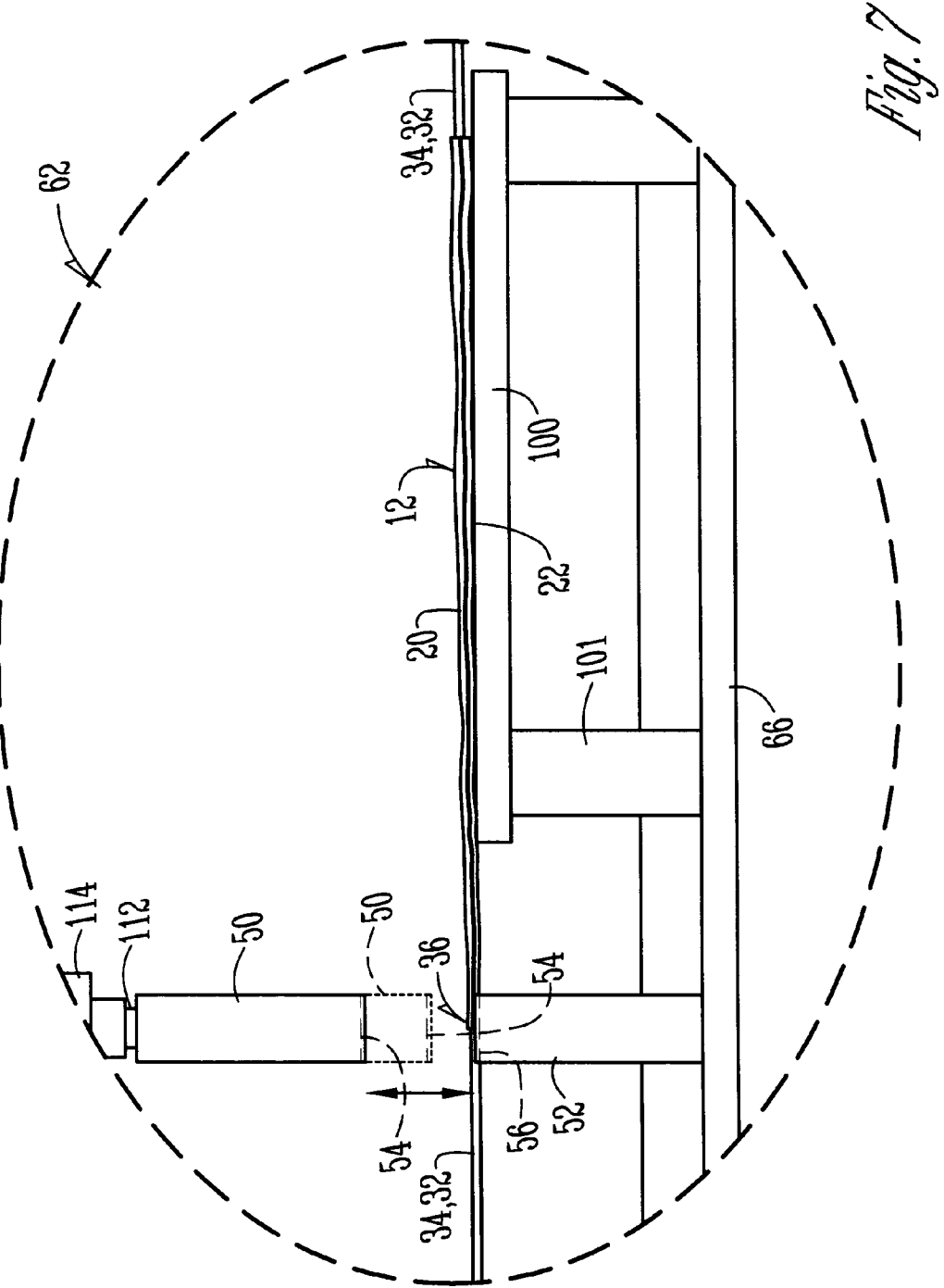
FIG. 7 is an enlarged view of the die station surrounded by line 7—7 of FIG. 4.

FIG. 4 shows the clamping surface 72 in its retracted position, and FIG. 3 shows the clamping surface 72 in its lowered clamped position. In this lowered position the clamping surface 72 engages the wire 34 and presses it against the clamping platform 74 to prevent movement of the wire.

Figure 8:
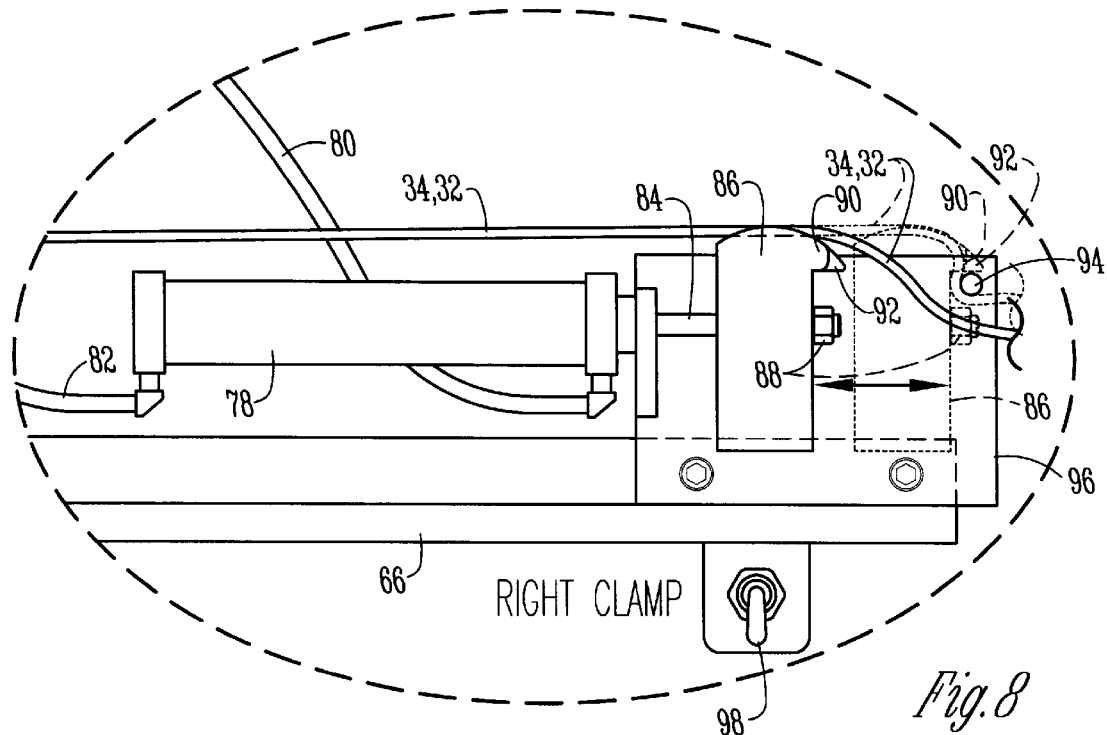
FIG. 8 is an enlarged view of the right-hand clamping station surrounded by line 8—8 of FIG. 4.
Figure 9:
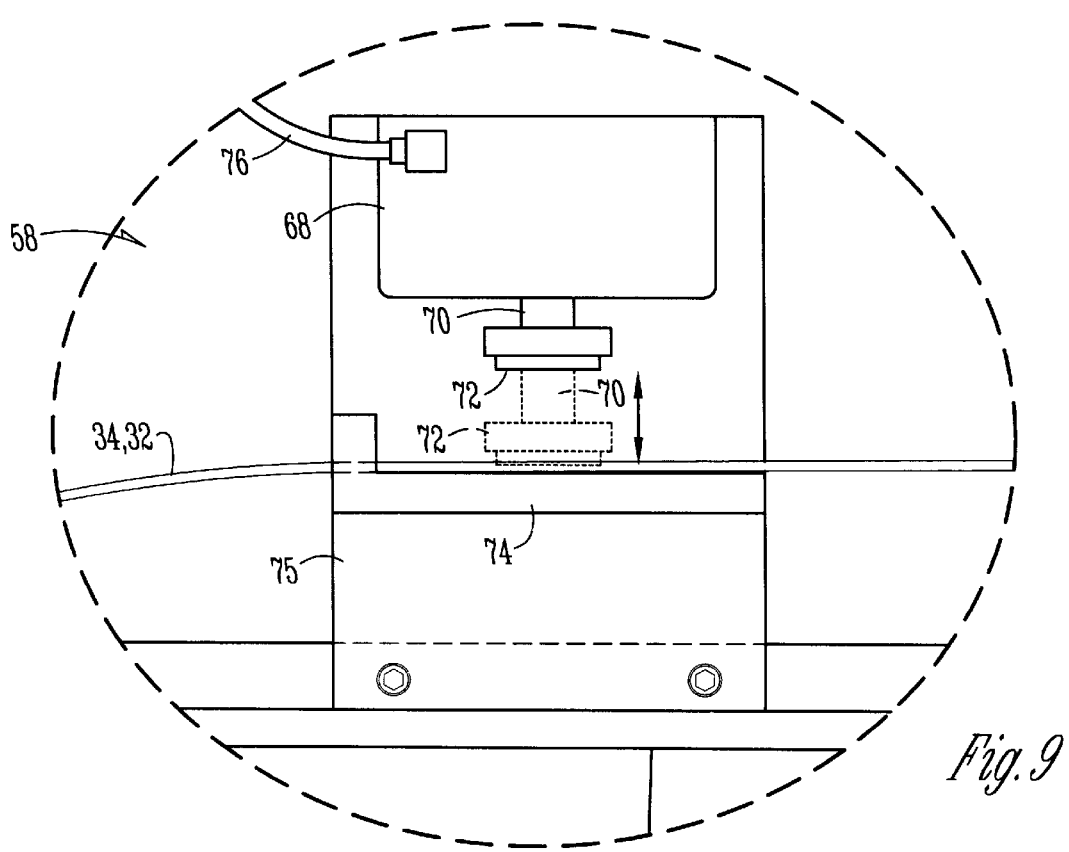
FIG. 9 is an enlarged view of the left-hand clamping station surrounded by line 9—9 of FIG. 4.

The right clamping station 60 includes a pneumatic cylinder 78 having a pneumatic tube 76 connected to one end and a pneumatic tube 80 connected to one end and another pneumatic tube 82 connected to the opposite end. Extending from pneumatic cylinder 78 is a ramrod 84 having a clamping head 86 thereon. FIG. 8 shows this clamping station 60 in more detail. The clamping head 86 is mounted on the ramrod 84 by means of a nut 88. Clamping head 86 includes a clamping lip 90 and a clamping groove 92 therein for receiving the wire 34. A clamping pin 94 is mounted on a clamping frame 96 which is attached to the support frame 66. A right clamp switch 98 is provided for actuating the pneumatic cylinder 78 to extend clamping head 86 from its retracted position shown in solid lines in FIG. 8 to its extended position shown in shadow lines in FIG. 8. In its extended position, the clamping lip 90 presses the wire against the clamping pin 94 and stretches the wire slightly so as to make it taut. When the left clamping station 58 and the right clamping station 60 are both in their clamped or extended positions, the wire 34 is held rigidly and taut, with the pouch 12 being located at the die station 62 as shown in FIGS. 3 and 4.

Die station 62 includes a pouch support platform 100 mounted on a supporting frame 101 which is attached to the frame 66. The upper die 54 is mounted to a die ram 112 which extends from a pneumatic die cylinder 114 (FIG. 7) mounted rigidly to the control console 74. Control console 74 is supported from support frame 66 by means of a support column 115.

On the face of console 64 is a left clamp switch 116 for operating the left clamp station 58. A seal pressure gauge 118 registers the pressure applied between the two dies 50, 52 in their clamping position. This pressure may be adjusted by an adjustment control (not shown) so as to achieve the desired pressure between the dies 50, 52 during the sealing process.

A clamp pressure gauge 120 registers the pneumatic pressure being provided at the left clamping station 58 and the right clamping station 60. This clamping pressure also may be adjusted by controls (not shown).

An upper die temperature adjustor is shown at 122 and a lower die temperature adjustor is shown at 124. These temperature controls permit adjustment of the temperature of the two dies so as to achieve the desired result.

In operation, the pouch 12 is placed on the support platform 100, with the sealing area 36 positioned between the two dies 52, 54. The wire 34 is placed beneath the clamping surface 72, and the cylinder 68 is actuated to force the clamping surface 72 down so as to hold the wire 34 in a stationary position.

Next, the wire 34 is placed around the clamping lip 90 of the clamping head 86, and beneath the clamping pin 94. The pneumatic cylinder is actuated to force the clamping head 86 to its extended position, thereby clamping the wire 34 against pin 94, and holding it taut.

Next, the pneumatic cylinder 114 is actuated to force the upper die 54 downwardly into sealing engagement with the sealing area 36. The die 54 has been preheated so as to apply both heat and pressure to the sealing area 36.

Using the present invention, the sealing area 36 can be sealed within a matter of seconds. There is no need to add any foreign materials such as glue, paper or other materials. The seal is provided by the plastic layer 42 on the interior surface of the walls 20, 22. In some cases, depending upon the heat and pressure applied, the insulation surrounding the wire is also partially melted so as to fuse together with the plastic layer 42 and provide a seal. Several factors contribute to the proper sealing at the sealing area 36. The pressure, heat, and time of compression during the die clamping process can vary depending upon the particular materials used. An example of a preferred combination of heat, pressure and time is as follows:

1. Pressure 20 PSI.
2. Heat of the top die 240° F.
3. Heat of the bottom die 240° F.
4. Time of clamping 7 seconds.

Other factors which may affect the sealing operation are the materials used for the insulation of the wires and also for the plastic layer 42 within the pouch 12. While various types of plastic may be used a preferred plastic for the insulation on the wire is an ethylene vinyl acetate copolymer supplied by Equistar Chemicals LP under the part number UE 631-000. This particular insulation has the following typical properties:

1. Vinyl acetate content 19%.
2. Melt index 2.3 g/10 minutes.
3. Density is 0.94 g/cc.
4. Tinsel strength, 2150 PSI.
5. Ultimate elongation, 710%.

The above properties may be varied without detracting from the invention.

The plastic layer 42 may be varied without detracting from the invention also. However, a preferred material for use as the plastic layer is a 26 pound per ream Surlyn®, manufactured by DuPont under the product number 1652-1. An alternate material for use in making the pouch 12 is a material supplied by Genesis Converting under the product number PF-100G, which includes a clear polyethylene layer for the layer 42.

Figure 11:
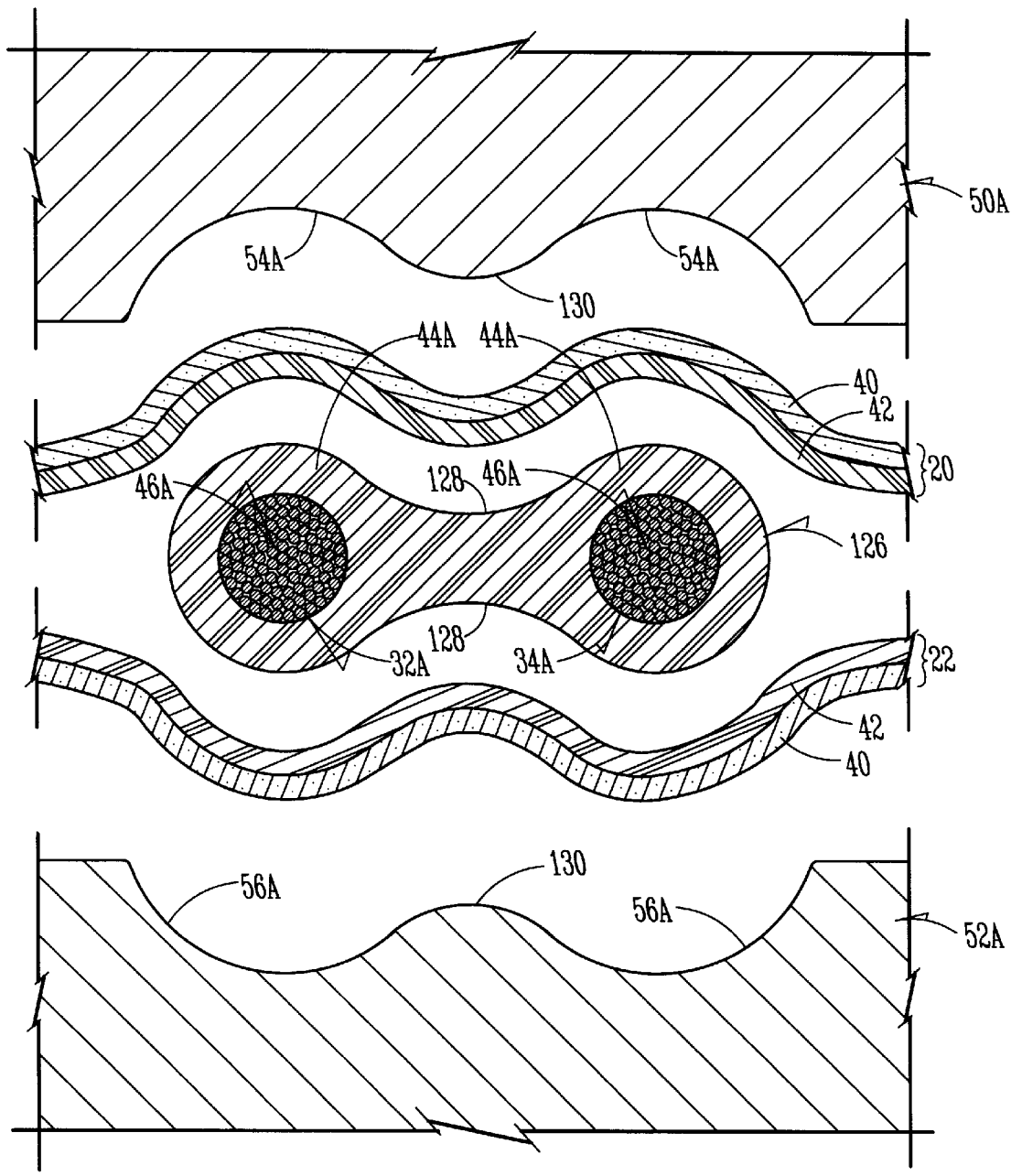
FIG. 11 is a view similar to FIG. 10, but showing the modified die configuration used for a different cross sectional configuration of wire.

Referring to FIG. 11, a modified wire configuration designated by the numeral 126 is shown. Wire 126 is a dual wire having two wire cores 46A surrounded by an insulation material 44A. The insulation material 44A provides a web 128 which joins the two wires 32A and 34A together.

The upper die 50A and lower die 52A are configured to conform to the outer shape of the dual wire 126. Upper die 50A includes two semicircular cavities 54A with a web node 130 positioned therebetween. The lower die 52A includes lower semicircular cavities 56A with a web node 130 positioned therebetween. When the upper and lower clamps 50A, 52A are pressed together, the web nodes 130 compress the web 128, while the cavities 54A, 56A compress the insulation around the wires 32A, 34A.

Other configurations of wire may be accommodated by changing the shape of the dies so that the dies apply pressure and heat to the sealing area 36 during the sealing process.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention as further defined in the following claims.

What is claimed is:

1. A method for packaging and using an electrode having a conductive hydrogel adapted to be placed in contact with a patient's skin and an electrical wire surrounded by a plastic insulation material, said electrical wire having a first end connected to said electrode, a second end connected to a plug, and an intermediate wire portion between said first and second ends of said wire, said method comprising:

placing said electrode within a pouch comprising at least first and second pouch walls which form a pouch enclosure that is completely enclosed except for an open sealing area between said first and second pouch walls, said pouch walls each having a plastic layer at said open sealing area;

extending said wire through said open sealing area to a position where said second end of said wire is outside said pouch enclosure, said first end of said wire is within said pouch enclosure and connected to said electrode, and said intermediate wire portion of said wire is positioned between said plastic layers of said first and second pouch walls at said sealing area;

fusing said plastic layers of said first and second pouch walls around and to said insulation material of said electrical wire to cause said electrode to be hermetically sealed within said pouch enclosure;

said fusing step comprising placing first and second dies on opposite sides of said sealing point with said walls of said pouch and said wire therebetween, compressing said first and second dies together with a predetermined pressure, and heating at least one of said first and second dies to a predetermined temperature so as to impart heat to said walls of said pouch and said wire during said compressing step;

plugging said plug into electrical apparatus at the time of use of said electrode while said intermediate portion of said wire is fused between said first and second pouch layers at said sealing area;

opening said pouch to gain access to said electrode within said pouch enclosure;

removing said electrode from said pouch;

placing said hydrogel of said electrode in contact with a patient's skin after removal of said electrode from said pouch.

2. A method according to claim 1 wherein said opening step comprises tearing said pouch walls.

3. A method according to claim 1 wherein said compressing step further comprises using said first and second dies each of which have recesses shaped to conform to the shape of said wire with said insulation material thereon and sized to apply pressure to said wire and said insulation material during said compressing step.

* * * * *